United States Patent
Afanasewicz et al.

(10) Patent No.: US 8,577,440 B2
(45) Date of Patent: Nov. 5, 2013

(54) METHOD AND SYSTEM FOR POSITIONING A SENSOR

(75) Inventors: Elizabeth A. Afanasewicz, Chestnut Hill, MA (US); Robert P. Harhen, Haverhill, MA (US); Adam J. Young, Dedham, MA (US); Rafael M. Cordero, Bedford, MA (US)

(73) Assignee: Covidien LP, Mansfield, MA (US)

( * ) Notice: Subject to any disclaimer, the term of this patent is extended or adjusted under 35 U.S.C. 154(b) by 259 days.

(21) Appl. No.: 13/074,127

(22) Filed: Mar. 29, 2011

(65) Prior Publication Data

US 2012/0253163 A1   Oct. 4, 2012

(51) Int. Cl.
*A61B 5/0478* (2006.01)
*A61B 5/0476* (2006.01)

(52) U.S. Cl.
USPC ............ 600/383; 600/391; 600/393; 600/544

(58) Field of Classification Search
USPC .................................. 600/383, 391–393, 544
See application file for complete search history.

(56) References Cited

U.S. PATENT DOCUMENTS

| | | | |
|---|---|---|---|
| 5,217,013 | A | 6/1993 | Lewis et al. |
| 5,584,296 | A | 12/1996 | Cui et al. |
| 5,830,137 | A | 11/1998 | Scharf |
| 6,032,064 | A | 2/2000 | Devlin et al. |
| 6,171,258 | B1 | 1/2001 | Karakasoglu et al. |
| 6,330,468 | B1 | 12/2001 | Scharf |
| 6,394,953 | B1 | 5/2002 | Devlin et al. |
| 6,654,626 | B2 | 11/2003 | Devlin et al. |
| 6,728,564 | B2 | 4/2004 | Lahteenmaki |
| 6,934,570 | B2 | 8/2005 | Kiani et al. |
| 6,934,571 | B2 | 8/2005 | Wiesmann et al. |
| 7,047,056 | B2 | 5/2006 | Hannula et al. |
| 7,130,673 | B2 * | 10/2006 | Tolvanen-Laakso et al. . 600/383 |
| 7,164,938 | B2 | 1/2007 | Geddes et al. |
| 7,215,994 | B2 * | 5/2007 | Huiku ........................... 600/544 |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Soto, Denise A.; "A Comparative Study of Pulse Oximeter Measurements: Digit Versus Earlobe," Master of Science Thesis, California State University Dominguez Hills, May 1997, 46 pgs.

(Continued)

*Primary Examiner* — Lee S Cohen
(74) *Attorney, Agent, or Firm* — Fletcher Yoder PC (57) ABSTRACT

Embodiments of the present disclosure relate to sensor designs or shapes configured to facilitate placement of sensor electrodes and, thus, proper positioning of the sensors on patients. According to certain embodiments, a sensor may include a substrate that includes multiple electrodes, where a first electrode is configured to be placed on a patient's temple and a second electrode is configured to be placed on a patient's forehead directly above a patient's eyebrow. The sensor may include a particular shape and a fixed distance between the first and second electrodes to facilitate proper angling and positioning of the first and second electrodes as well as the other electrodes (e.g., third and fourth electrodes). Other embodiments may include a method for positioning the sensor on the patient, including a monitor with help screens.

24 Claims, 8 Drawing Sheets

(56) References Cited

U.S. PATENT DOCUMENTS

| | | | |
|---|---|---|---|
| 7,257,438 | B2 | 8/2007 | Kinast |
| 7,289,837 | B2 | 10/2007 | Mannheimer et al. |
| 7,297,119 | B2 | 11/2007 | Westbrook et al. |
| 2002/0019588 | A1 | 2/2002 | Marro et al. |
| 2003/0225323 | A1 | 12/2003 | Kiani et al. |
| 2004/0117891 | A1 | 6/2004 | Hannula et al. |
| 2004/0260161 | A1 | 12/2004 | Melker et al. |
| 2004/0267104 | A1 | 12/2004 | Hannula et al. |
| 2005/0059869 | A1 | 3/2005 | Scharf et al. |
| 2005/0070776 | A1 | 3/2005 | Mannheimer et al. |
| 2005/0277819 | A1 | 12/2005 | Kiani et al. |
| 2005/0283082 | A1 | 12/2005 | Geddes et al. |
| 2006/0064024 | A1 | 3/2006 | Schnall |
| 2006/0195028 | A1 | 8/2006 | Hannula et al. |
| 2006/0258930 | A1 | 11/2006 | Wu et al. |
| 2006/0264722 | A1 | 11/2006 | Hannula et al. |
| 2006/0264723 | A1 | 11/2006 | Hannula et al. |
| 2006/0264724 | A1 | 11/2006 | Hannula et al. |
| 2006/0264725 | A1 | 11/2006 | Hannula et al. |
| 2006/0264727 | A1 | 11/2006 | Mannheimer et al. |
| 2006/0281984 | A1 | 12/2006 | Mannheimer et al. |
| 2007/0142715 | A1 | 6/2007 | Banet et al. |
| 2007/0208269 | A1 | 9/2007 | Mumford et al. |
| 2008/0154111 | A1 | 6/2008 | Wu et al. |
| 2008/0221413 | A1 | 9/2008 | Hoarau |
| 2008/0228053 | A1 | 9/2008 | Wang et al. |
| 2008/0316488 | A1 | 12/2008 | Mao et al. |
| 2009/0105577 | A1 | 4/2009 | Wu et al. |
| 2011/0190600 | A1* | 8/2011 | McKenna et al. ............ 600/301 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| FR | 2685865 | 7/1993 |
| JP | 6014906 | 1/1994 |
| JP | 2004148069 | 5/2004 |
| JP | 2006122458 | 5/2006 |
| JP | 2006201114 | 8/2006 |
| JP | 2006239267 | 9/2006 |
| WO | WO9502358 | 1/1995 |
| WO | WO9736536 | 10/1997 |

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Hall, J.D., et al.; "Bispectral index: comparison of two montages", *British Journal of Anaesthesia* 1998; 80: 342-344.

DeKock, Marc; "Pulse Oximetry Probe Adhesive Disks: a Potential for Infant Aspiration," *Anesthesiology*, vol. 89, pp. 1603-1604 (1998).

Rohling, Roman, et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Gosney, S., et al.; "An alternative position for the pulse oximeter probe," *Anaesthesia*, vol. 56, p. 493 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of esophageal photoplethysmographic signals and blood oxygen saturation measurements in cardiothoracic surgery patients," *Physiological Measurement*, vol. 23, No. 3, pp. 533-545 (Aug. 2002).

Irie, A., et al., "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Manberg, Paul J., Ph.D..; Letters to the Editor "BIS Monitoring Requires Proper Electrode Placement for Optimum Performance", *Anesth Anag* 2003; 97:1206.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Bentley, David J. et al.; "Measure Pressure with Thin Film"; Paper Film & Foil Converter; May 1, 2003.

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Kocher, Serge, et al.; "Performance of a Digital $PCO_2/SPO_2$ Ear Sensor," *Journal of Clinical Monitoring and Computing*, vol. 18, pp. 75-59 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Shiraishi, Toshie, et al.; "A Comparison of Frontal and Occipital Bispectral Index Values Obtained During Neurosurgical Proceduresm", *Anesth Analg*. 2004; 98:1773-5.

Author Unknown; "Aspect Medical Systems Operating Manual", copyright 2006, 102 pages.

(56) References Cited

OTHER PUBLICATIONS

Dahaba, Ashraf A., et al.; "BIS-VistaTM Occipital Montage in Patients Undergoing Neurosurgical Procedures during Propofol-Remifentanil Anesthesia", *Anesthesiology*, 2010: 112645-51.

Author Unknown; "BIS-VistaTM Monitoring System Bilateral Monitoring Addendum", Aspect Medical Systems, Inc., copyright 2010, 22 pages.

Hayoz, J., et al.; "World's First Combined digital Pulse Oximetry Pulse Oximetry and Carbon Dioxide Tension Ear Sensor", *Abstracts*, A6, p. S103. (undated).

http://www.fcw.com.my/fujifilm.html.

"BIS Integrated Solutions"; Phillips, Inc. (2006), 2 pages.

"Aspect Medical Systems Continuum of Care"; Anandic Medical Systems (2006), 17 pages.

* cited by examiner

STEP 1 : POSITION ELECTRODE 1 ON
TEMPLE BETWEEN CORNER OF EYE AND HAIRLINE

FIG. 11

STEP 2 : POSITION ELECTRODE 2
DIRECTLY ABOVE EYEBROW

METHOD AND SYSTEM FOR POSITIONING A SENSOR

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as electroencephalography (EEG), and the devices built based upon electroencephalographic techniques are commonly referred to as EEG monitors. EEG monitors use non-invasive electrophysiological monitoring to evaluate global changes in a patient's condition, for example, during surgical procedures. Examples of global changes may include assessing the effects of anesthetics, evaluating asymmetric activity between the left and right hemispheres of the brain in order to detect cerebral ischemia, and detecting burst suppression. One such technique includes bispectral index (BIS) monitoring to measure the level of consciousness by algorithmic analysis of a patient's EEG during general anesthesia.

Often the monitoring devices, or probes or sensors associated with the monitoring devices, are applied to the patient. For example, electrodes for use with the EEG monitors may be applied to the temple and forehead of the patient. For example, sensors for BIS monitoring may include a single strip that includes three or four electrodes for placement on the forehead to noninvasively acquire an EEG signal. Proper placement of the electrodes of the sensor helps to correctly calculate the physiological characteristics (e.g., BIS). Misplacement of the electrodes may increase the algorithmic work, filtering, and artifacting to obtain the physiological characteristics, which may result in potentially misreporting the physiological characteristics.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or inure specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is generally directed to sensor designs or shapes for electroencephalography (EEG) sensors that include features to ensure proper placement of electrodes of each EEG sensor on a temple and forehead of a patient. In addition, the sensor designs or shapes may improve and maintain adhesion of the electrodes to the temple and forehead. As discussed herein, the sensor designs or shapes are configured to help in the angular placement of the electrodes and to facilitate proper positioning of the sensor. For example, some of the features of the sensor design or shape may include fixed distances between particular electrodes or more pronounced curvatures. Also, as discussed herein, the sensor designs or shapes are configured to help maintain adhesion to the patient's temple and forehead. Some of the features of the sensor design or shape may include protrusions from the electrodes configured with edges to better grip the skin. In this manner, the sensor may be properly adhered to the patient's temple and forehead to allow the accurate obtainment of physiological data such as an EEG signal, for example, for bispectral index (BIS) monitoring.

Figure 1:
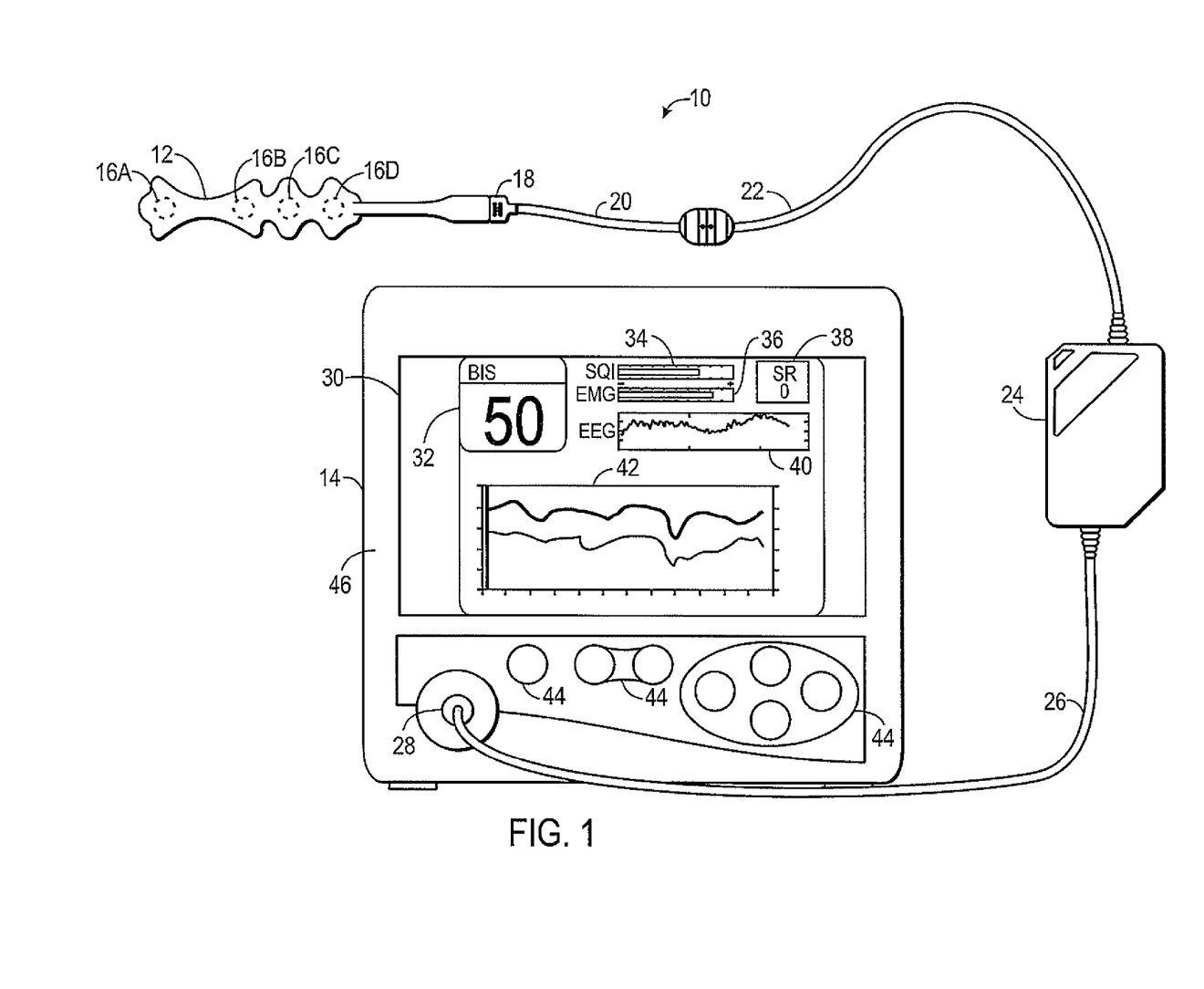
FIG. 1 is a front view of an embodiment of a monitoring system.

With the foregoing in mind, FIG. 1 is a front view of an embodiment of a patient monitoring system 10. The monitoring system 10 may include a sensor 12 and an EEG monitor 14. The sensor 12 may include electrodes 16 (e.g., four electrodes 16A, 16B, 16C, and 16D) that are self adherent and self prepping to temple and forehead areas of a patient and that are used to acquire EEG signals. The sensor 12 may be coupled through connector 18 to a cable 20 (e.g., patient interface cable), which in turn may be coupled to a cable 22 (e.g., pigtail cable). In certain embodiments, the sensor 12 may be coupled to the cable 22 thereby eliminating the cable 20. The cable 22 may be coupled to a digital signal converter 24, which in turn is coupled to the cable 26 (e.g., monitor interface cable). In certain embodiments, the digital signal converter 24 may be embedded in the monitor 14 to eliminate the cables 22 and 26. Cable 26 may be coupled to the monitor 14 via a port 28 (e.g., digital signal converter port).

The monitor 14 may be capable of calculating physiological characteristics relating to the EEG signal received from the sensor 12. For example, the monitor may be capable of algorithmically calculating BIS from the EEG signal. BIS is a measure of a patient's level of consciousness during general anesthesia. Further, the monitor 14 may include a display 30 capable of displaying the physiological characteristics, historical trends of physiological characteristics, other information about the system (e.g., instructions for placement of the sensor 12 on the patient), and/or alarm indications. The monitor 14 may display a patient's BIS value 32. The BIS value 32 represents a dimensionless number (e.g., ranging from 0, i.e., silence, to 100, i.e., fully awake and alert) output from a multivariate discriminate analysis that quantifies the overall bispectral properties (e.g., frequency, power, and phase) of the EEG signal. For example, a BIS value 32 between 40 and 60 may indicate an appropriate level for general anesthesia. The monitor 14 may also display a signal quality index (SQI) bar graph 34 (e.g., ranging from 0 to 100) which measures the signal quality of the EEG channel source(s) based on impedance data, artifacts, and other variables. The monitor 14 may yet also display a electromyograph (EMG) bar graph 36 (e.g., ranging from 30 to 55 decibels) which indicates the power (e.g., in decibels) in the frequency range of 70 to 110 Hz. The frequency range may include power from muscle activity and other high-frequency artifacts. The monitor 14 may further display a suppression ratio (SR) 38 (e.g., ranging from 0 to 100 percent) which represents the percentage of epochs over a given time period (e.g., the past 63 seconds) in which the EEG signal is considered suppressed (i.e., low activity). In certain embodiments, the monitor 14 may also display a burst count for the number of EEG bursts per minute, where a "burst" is defined as a short period of EEG activity preceded and followed by periods of inactivity or suppression. The monitor 14 may yet further display the EEG waveform 40. In certain embodiments, the EEG waveform 40 may be filtered. The monitor 14 may still further display trends 42 over a certain time period (e.g., one hour) for EEG, SR, EMG, SQI, and/or other parameters. As described below, in certain embodiments, the monitor 14 may display stepwise instructions for placing the sensor 12 on the patient. In addition, the monitor 14 may display a verification screen verifying the proper placement of each electrode 16 of the sensor 12 on the patient. In certain embodiments, the monitor 12 may store instructions on a memory specific to a specific sensor type or model. In other embodiments, the sensor 12 may include a memory that provides the instructions to the monitor 14.

Additionally, the monitor 14 may include various activation mechanisms 44 (e.g., buttons and switches) to facilitate management and operation of the monitor 14. For example, the monitor 14 may include function keys (e.g., keys with varying functions), a power switch, adjustment buttons, an alarm silence button, and so forth. It should be noted that in other embodiments, the parameters described above and the activation mechanisms 44 may be arranged on different parts of the monitor 14. In other words, the parameters and activation mechanisms 44 need not be located on a front panel 46 of the monitor 14. Indeed, in some embodiments, activation mechanisms 44 are virtual representations in a display or actual components disposed on separate devices. In addition, the activation mechanisms 44 may allow selecting or inputting of a specific sensor type or model in order to access instructions stored within the memory of the monitor 12.

The design or shape of the embodiments of the sensors 12 described below may include features to help facilitate the proper placement of the electrodes 16, and thus the sensor 12, on the patient's temple and forehead. For example, the electrodes 16 may be at fixed distances with respect to each other to allow for conformity in the diagonal placement of the electrodes 16. In particular, the electrodes 16A and 16B may include a bridge of sufficient width and rigidity to fix the distance between these electrodes 16A and 16B and to prevent lateral movement along a longitudinal axis of the sensor 12. Also, the bridge may include a curvature of a concave nature configured to trace up and around the lateral and top edges of the patient's eyebrow to reinforce correct placement of the electrodes 16A and 16B. In addition, the sensor 12 may include labels or other features (e.g., arrows) to facilitate the proper placement of the electrodes 16. Further, the design or shape of the sensor 12 may include features to prevent the sensor from lifting from the patient's skin. For example, the areas of sensor 12 surrounding one or more electrodes 16 may include protrusions or tabs to counteract peeling forces and to reduce adhesion shear. Also, a tail section of the sensor 12 configured to connect with the cables described above may include a narrow tail section to prevent the twisting of the tail section and the potential marking of the patient's skin.

Figure 2:
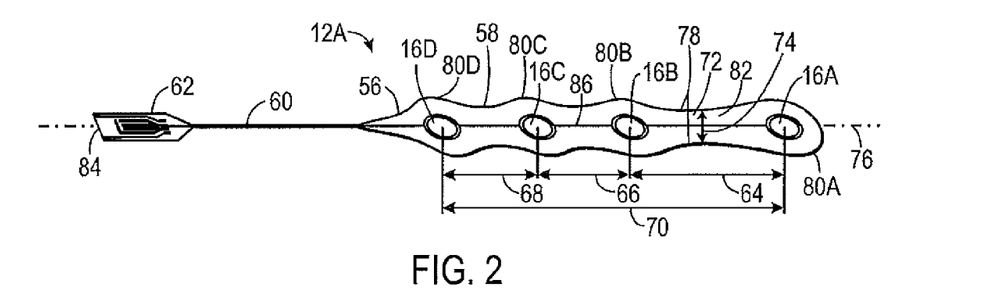
FIG. 2 is a bottom perspective view of an embodiment of a sensor of the monitoring system of FIG. 1.

FIG. 2 illustrates some of the features that help facilitate the proper placement of the sensor 12A and maintain proper adhesion of the sensor 12A to the patient's skin. For example, the sensor 12A may include fixed distances between the electrodes 16, a bridge 72 of sufficient width and rigidity to maintain the fixed distance between the electrodes 16A and 16B, a concave curvature 78 to help facilitate placement of electrodes 16A and 16B, protrusions 80 to maintain adherence of the electrodes 16A and 16B to the patient's skin, and a narrow tail section 60.

More specifically, the sensor 12A may include a substrate 56 (e.g., an elongated substrate) that includes a main body 58, a tail section 60 coupled to the second end portion, and a connector 62 coupled to the main body 58 via the tail section 60. As illustrated, the substrate 56 may have a length (e.g., along a longitudinal axis 76), a width (e.g., width 74), and a thickness, wherein the length is substantially greater than the width and the width is substantially greater than the thickness. The substrate 56 may be substantially rigid in a direction along its width and substantially flexible in a direction along its thickness (e.g., to facilitate bending of the substrate 56 about a patient's head). The main body 58, as illustrated, may include four electrodes 16 (e.g., 16A, 16B, 16C, and 16D) with electrode 16A located on a first end portion of the body 58 and electrode 16D located on a second end portion of the body 58. The electrodes 16 may be configured to be positioned at an angle as follows: electrode 16D positioned approximately 3 inches (5 cm) above the bridge of the patient's nose, electrode 16B positioned directly above the patient's eyebrow, and electrode 16A positioned on the patient's temple horizontally even with the corner of the patient's eye and vertically centered between the corner of the patient's eye and the patient's hairline. The inclusion of four electrodes 16 may be configured for a BIS montage to monitor physical characteristics of the patient. For example, electrodes 16A and 16D may be configured to measure BIS, the electrode 16B configured to determine eye blinks (i.e., motion artifacts), and electrode 16C configured to act as a ground.

As mentioned above, the design or shape of the sensor 12A may include features to help facilitate the proper placement of the electrodes 16, and thus the sensor 12, on the patient's temple and forehead. For example, the electrodes 16 may be at fixed distances with respect to each other to allow for conformity in the placement of the electrodes 16. The distances mentioned below may be based on an average head size of a group of adults including males and females, but it should be understood that other criteria to determine the fixed distances may be used. For example, the distances may be determined based on an average head size for a neonate, or based on small, medium, and large head sizes. The electrodes 16A and 16B may include a fixed distance 64 to allow for conformity in the diagonal placement of the electrodes 16A and 16B. For example, the fixed distance 64 may be 1.9 inches between the respective centers of the electrodes 16A and 16B. Electrodes 16B and 16C may also include a fixed distance 66, for example of approximately 1.1 inches, between their respective centers. Electrodes 16C and 16D may include a fixed distance 68, for example of approximately 1.1 inches, between their respective centers. In certain embodiments, the distances 66 and 68 may differ from each other to accommodate for different head sizes. Overall, electrodes 16A and 16D may include a fixed distance 70 (e.g., a distance substantially equal to a distance from a patient's temple to a central portion of the patient's forehead), for example of approximately 4.2 inches, between their respective centers to allow for conformity in the diagonal placement of the sensor 12A.

In addition, the main body 58 may include a bridge 72 spanning between electrodes 16A and 16B of sufficient stiffness or rigidity to help fix the distance 64 between the electrodes 16A and 16B. The bridge 72 may also include a width 74 sufficient to prevent excessive lateral movement along a longitudinal axis 76 of the sensor 12 between electrodes 16A and 16B, but not cover the eyebrow and lateral hairline of most patients.

Additionally, the main body 58 maybe shaped to facilitate the proper placement of the sensor 12A. In particular, the bridge 72 may include a curvature 78 to reinforce the proper placement of sensor 12A. In particular, the curvature 78 may be of a concave nature configured to trace up and around the lateral and top edges of the patient's eyebrow to reinforce correct placement of the electrodes 16A and 16B.

The main body 58 of the sensor 12A may include features to maintain proper adhesion of the sensor 12A to the patient's skin. In particular, the substrate 56 surrounding each electrode 16 may include protrusions 80 (80A, 80B, 80C, and 80D) from the main body 58. These protrusions 80 may counteract peeling forces and reduce adhesion shear as described in greater detail below.

Additionally, the design or shape of the sensor 12 may include a narrow tail section 60 coupled to the second end portion of the main body 58. The narrow tail section 60 may minimize any twisting action of the section 60 due to the weight of the cables described above and coupled to the sensor 12 at the connector 62. Minimizing twisting action of the tail section 60 may reduce potential marking of the patient's skin.

As to the other components and composition of the sensor 12A, the electrodes 16 may be formed from a suitable conductive composition, such as a metal or alloy (e.g., silver/silver chloride, copper, aluminum, gold, or brass) or a conductive polymer (such as screen-printable silver/silver chloride inks carbon impregnated polymers). A suitable material for the substrate 56 may include polyester. Other examples of suitable materials for forming the substrate 56 may include, but are not limited to, rubber or elastomeric compositions (including acrylic elastomers, polyimide, silicones, silicone rubber, celluloid, PMDS elastomer, polyurethane, polypropylene, acrylics, nitrile, PVC films, acetates, and latex). The substrate 56 may include a flexible circuit 82 including conductors 84 formed of a suitable material, such as a metal (e.g., silver or silver chloride). In certain embodiments, the conductors 84 may be routed from individual electrodes 16 of the sensor 12A to the connector 62. The connector 62 may be configured to couple the sensor 12A to one or more cables as described above. As illustrated, the sensor 12A may also include a conductive trace 86, such as a common conductor or wire, to allow a voltage to be sensed by each electrode 16. The sensor 12A may also include an adhesive backed foam layer over the entire substrate 56 or only a portion of the substrate 56. The sensor 12A may further include an adhesive layer over the main body 58 of the substrate 56 configured to facilitate adhesion or attachment of the sensor 12A to a patient's skin.

Figure 3:
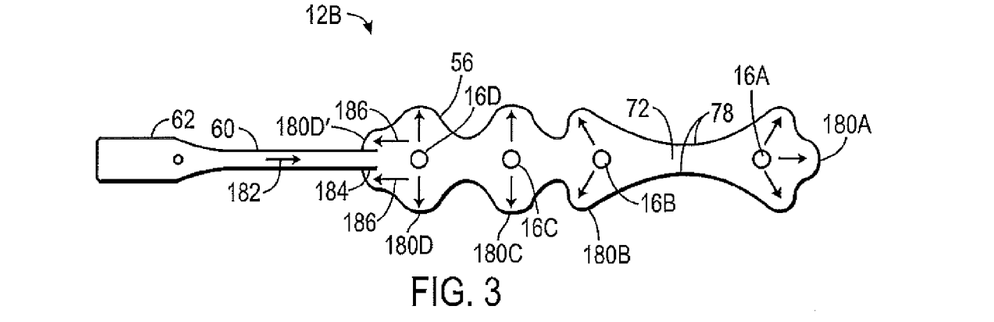
FIG. 3 is a top view of another embodiment of a sensor of the monitoring system of FIG. 1.

To help facilitate the proper placement of the sensor 12B and maintain proper adhesion of the sensor 12B to the patient's skin, the sensor 12B, as illustrated in FIG. 3, may include additional features. The sensor 12B in FIG. 3 is generally as described in FIG. 2. For example, the sensor 12B may include the narrow tail section 60 and the fixed distance (including the stiff bridge 72) between electrodes 16A and 16B. However, the sensor 12B may include additional features to facilitate proper placement of the sensor 12B and to improve and maintain the adhesion of the sensors 12B to the patient. For example, the sensor 12B may include a more pronounced concave curvature 78 than the sensor 12A in FIG. 2. The more pronounced curvature 78 may further facilitate and reinforce correct placement of the electrodes 16A and 16B. In particular, the curvature 78 may trace above the top edge of the patient's eyebrow and wrap around to the temple area.

In addition, each electrode 16 may include more pronounced protrusions 180 than the protrusions 80 in FIG. 2 to improve and maintain adherence of the electrodes 16 to the patient. For example, the substrate 56 surrounding electrode 16A may include protrusions 180A. The substrate 56 surrounding electrode 16B may include protrusions 180B, while the substrate 56 surrounding electrode 16C may include protrusions 180C. The substrate 56 surrounding electrode 16D may include protrusions 180D. The protrusions 180 may provide edges that grip or adhere better to the patient's skin than when the substrate 56 surrounding the electrodes 16 is generally rounded or circular as in FIG. 2. In particular, the protrusions 180 may help reduce adhesion shear by distributing load in different directions as indicated by the arrows. In addition, protrusions 180D of the sensor 12B may be configured to counteract a 180 degree peel of the sensor 12B in direction 182 due to lift-off of the tail section 60. In particular, the protrusions 180D' about electrode 16D may include a knife-cut 184 to separate the tail section 60 from the protrusions 180D. In particular, the knife-cut 184 provides forces in direction 186 to counteract lift-off of the protrusions 180D' caused by movement of the tail section 60.

Figure 4:
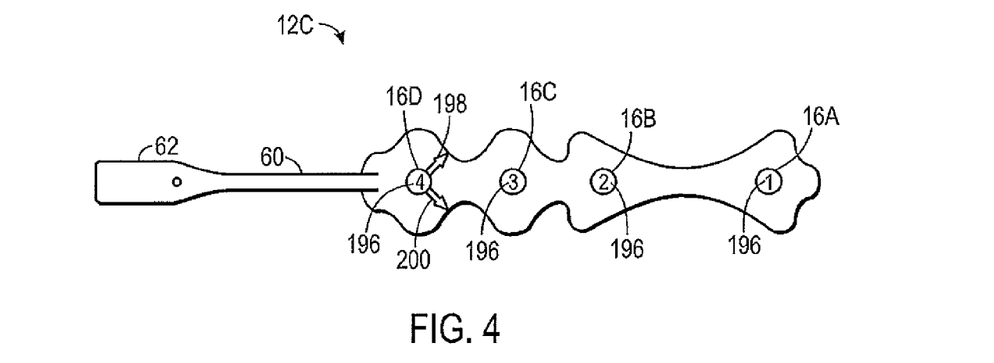
FIG. 4 is a top view of an embodiment of the sensor of FIG. 3.

To further facilitate the placement of the sensor 12, in particular the individual electrodes 16, the sensor 12 may include labels and/or alignment features such as those illustrated in sensor 12C of FIG. 4. The features illustrated on sensor 12C may be included with any of the embodiments of the sensor 12. In FIG. 4, the sensor 12C is as described above in FIG. 3. In addition, each individual electrode 16 of the sensor 12C may include a different label 196 to help a user distinguish the electrodes 16 from each other. The labels 196 may facilitate the placement of the electrodes 16 in accordance with instructions provided by the sensor manufacturer or on the monitor 14 as described in greater detail below. As illustrated, the label 196 may include numeric values. For example, numbers 2, 3, and 4 may designate forehead electrodes 16B, 16C, and 16D, respectively, while number 1 may designate temple electrode 16A. Alternatively, the label 196 may include letters, shapes, colors, or any combination thereof, to distinguish the electrodes 16.

Further, the sensor 12C may include arrows 198 and 200 to help in the placement of electrode 160. Alternatively, instead of the arrows 198 and 200, the electrode 16D may include some form of lines or projections to help in aligning the electrode 16D. The arrow 198 or another alignment feature may facilitate the positioning of the electrode 16D by aligning the arrow 198 with the center of the bridge of the patient's nose approximately as illustrated in FIG. 5.

Figure 5:
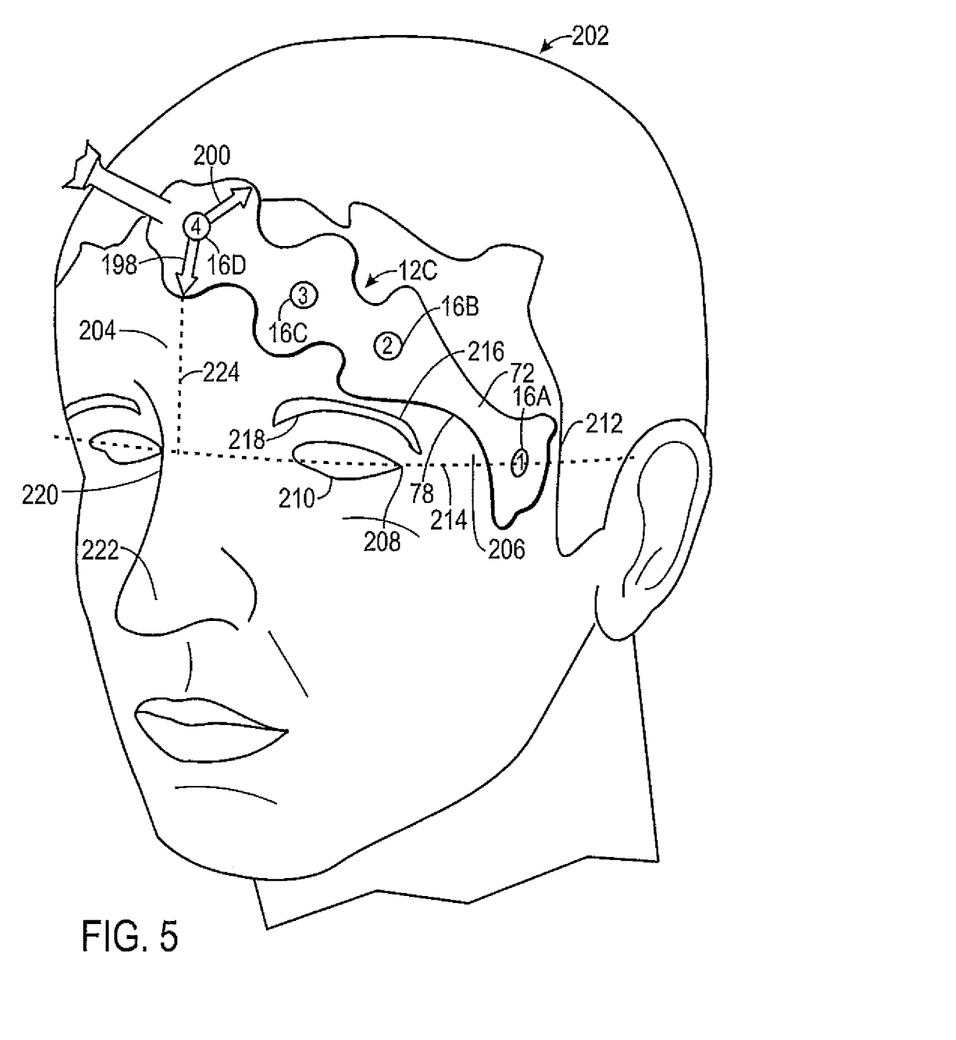
FIG. 5 is a perspective view of the sensor of FIG. 4 coupled to a patient illustrating an embodiment for sensor placement.
Figure 6:
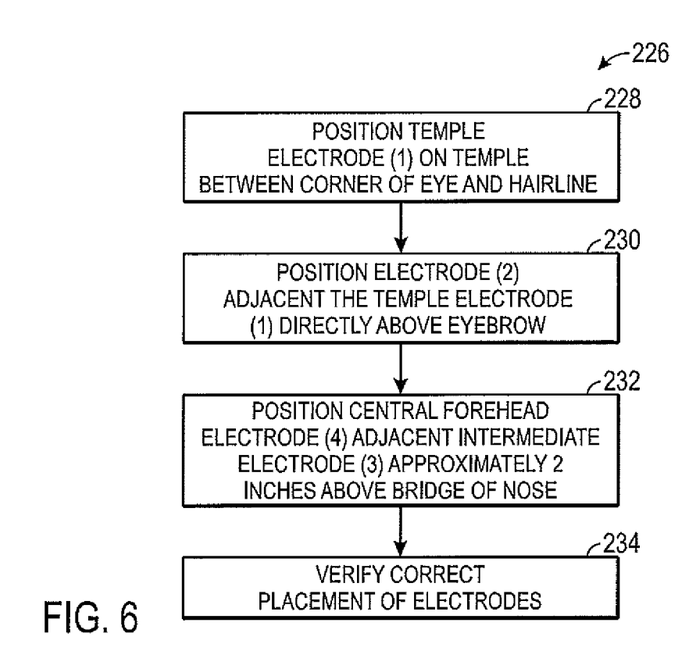
FIG. 6 is a flow chart depicting an embodiment of a method for positioning the sensor of FIG. 4 on the patient.

The sensor 12C in FIG. 5 illustrates the proper placement of sensor 12C on the patient 202 at an angle as described in a method 226 illustrated in FIG. 6. The method 226 or instructions similar to the method 226 may be provided separately with the sensor 12C by the sensor manufacturer. Alternatively, the instructions may be provided in a stepwise manner on the display 32 of the monitor 14.

As mentioned above, the electrodes 16B, 16C, and 16D may be configured for attachment to a patient's forehead 204, while the electrode 16A may be configured for attachment to the patient's temple 206. In general, the method 226 may begin by positioning temple electrode 16A (e.g., labeled 1) on the patient's temple 206 between a corner 208 of the patient's eye 210 and a patient's hairline 212 (block 222). As illustrated in FIG. 5, the electrode 16A is positioned on the patient's temple 206 approximately horizontally even with the corner 208 of the patient's eye 210 as indicated by dashed line 214 and approximately vertically centered between the corner 208 of the patient's eye 210 and the patient's hairline 212. Upon attaching electrode 16A to the temple 206, the method 226 may include positioning electrode 16B (e.g., labeled 2) adjacent temple electrode 16A directly above a top edge 216 of an eyebrow 218 (block 230). As mentioned above, the curvature 78 of the bridge 72 may trace above the top edge 216 of the patient's eyebrow 218 and wrap around to the temple area 206. Upon attaching electrode 16B above the eyebrow 218, the method 226 may include positioning central forehead electrode 16D (e.g., labeled 4) adjacent electrode 16B (e.g., labeled 3) at a center of the forehead 204 approximately 2 inches (5 cm) above a bridge 220 of the nose 222 (block 232). Positioning of the electrodes 16B and 16D may determine the position of electrode 16C by default. The illustrated placement of the sensor 12C may include a montage for BIS monitoring. With the proper placement of the sensor 12C, the arrow 198 may align with the bridge 220 of the patient's nose 222 as indicated by dashed line 224.

Upon placement of the electrodes 16A, 16B, 16C, and 16D, the method 226 may include verifying correct placement of the electrodes 16A, 16B, 16C, and 16D (block 234). Verification may include manually checking that the electrodes 16A, 16B, 16C, and 16D were properly placed in accordance with the instructions. For example, verification may include ensuring that arrow 198 of electrode 16D aligns with the bridge 220 of the nose 222, checking that electrode 16D is approximately 2 inches (5 cm) above the bridge 220 of the nose 222, and/or that electrode 16A is horizontally aligned with the corner 208 of the eye 210 between the corner 208 and the hairline 212. Alternatively, the monitor 14 may verify the placement of the electrodes 16A, 16B, 16C, and 16D automatically or in response to a request to check the placement of the sensor 12C as described in greater detail below.

Figure 7:
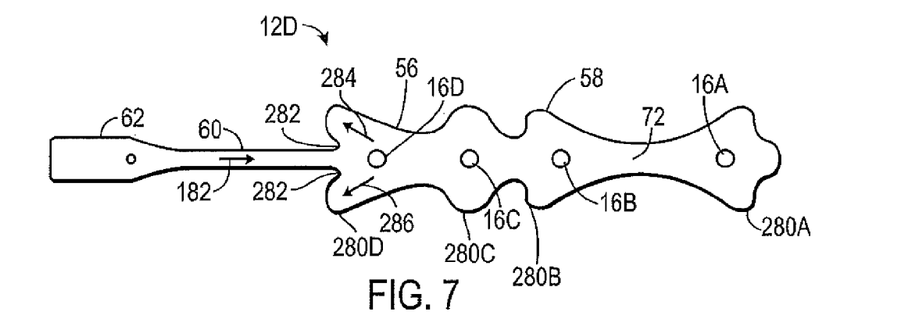
FIG. 7 is a is a top view of yet another embodiment of a sensor of the monitoring system of FIG. 1.

The sensor 12 may include additional features to facilitate the proper placement of the sensor 12 and maintain proper adhesion of the sensor 12 to the patient's skin. For example, the sensor 12D, as illustrated in FIG. 7, may include a different number and shape of protrusions 280 surrounding the electrode 16D. The substrate 56 surrounding electrodes 16A, 16B, 16C, and 16D may include protrusions 280A, 280B, 280C, and 280D, respectively. In particular, these protrusions 280 may help reduce adhesion shear by distributing load in different directions as previously described. In addition, protrusion 280D of the sensor 12D may be configured to counteract a 180 degree peel of the sensor 12D in direction 182 due to lift-off of the tail section 60. In particular, the protrusion 280D may include a radiused cut out 282 that tends to and keep the sensor 12D in place if the tail section 60 lifts off. Indeed, the protrusion 280D may provide forces in directions 284 and 286 to counteract lift-off of tail section 60.

Figure 8:
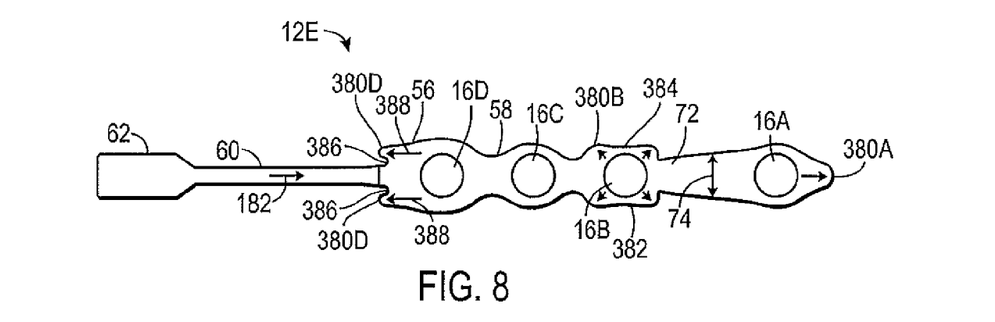
FIG. 8 is a top view of a further embodiment of a sensor of the monitoring system of FIG. 1.

Alternatively, the sensor 12 may include alternative shapes for the features. For example, the sensor 12E, as illustrated in FIG. 8, may include a different number and shape of protrusions 380 surrounding the electrodes 16. As illustrated, a single protrusion 380A may extend from the substrate 56 surrounding electrode 16A. The substrate 56 surrounding electrode 16B may include a rectangular shape with slightly concaved sides 382 and 384 to form protrusions 380B. Also, the substrate 56 surrounding electrode 16 D includes protrusions 380D. As above, the sensor 12E may include the protrusions 380 to improve and maintain adherence of the electrodes 16 to the patient. In particular, these protrusions 380 may help reduce adhesion shear by distributing load in different directions as indicated by the arrows. For example, protrusions 380D, as above, may be configured to counteract a 180 degree peel of the sensor 12E in direction 182 due to lift-off of the tail section 60. In particular, the substrate 56 includes a radiused cut-out 386, as above, to separate protrusions 380D and keep the sensor 12E in place if the tail section 60 lifts off. However, protrusions 380D may be oriented in direction 388 to provide forces directly opposed to a peel in direction 128 to counteract lift-off of tail section 60. Also, in contrast to above embodiments of the sensor 12, the bridge 72 increases in width 74 from electrode 16B to electrode 16A.

Figure 9:
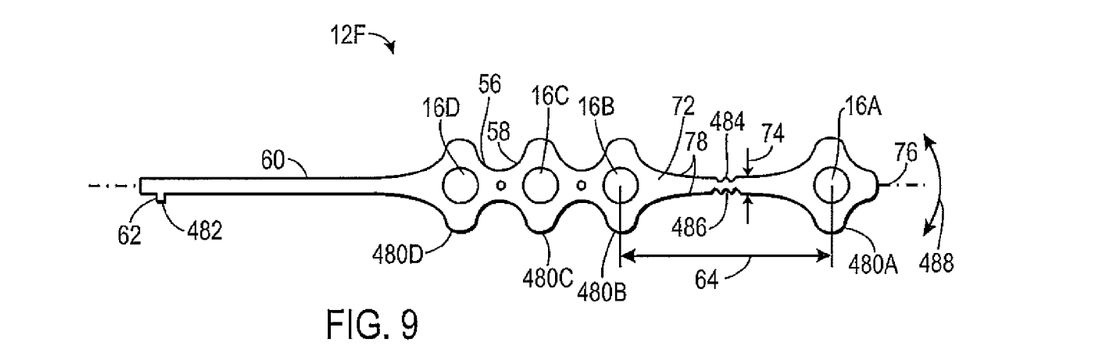
FIG. 9 is a top view of a yet further embodiment of a sensor of the monitoring system of FIG. 1.

The design or shape of the sensor 12F, illustrated in FIG. 9, may include differences from the above embodiments. For example, the connector 62 may include a tab 482. Also, the substrate 56 surrounding the electrodes 16 may include protrusions 480 that distribute load in different directions as indicated by the arrows. In particular, protrusions 480B and 480D surrounding electrodes 16B and 16D distribute the load differently than the above embodiments of the sensors 12.

Some of the differences may include features to further facilitate the proper placement of the sensor 12F on the patient. For example, the width 74 of the bridge 72 may be narrower than the bridge 72 in the other embodiments of the sensors 12 above resulting in a more pronounced concave curvature 78. The more pronounced concave curvature 78 may reinforce the correct placement of the electrodes 16A and 16B. For example, the curvature 78 may trace above the top edge of the patient's eyebrow and wrap around to the temple area.

In addition, the bridge 72 may include notches 484 disposed approximately at a mid-portion 486 of the bridge 72. As mentioned above, the bridge 72 may include sufficient stiffness or rigidity to help fix the distance 64 between the electrodes 16A and 16B, as well as sufficient width 74 to prevent excessive lateral movement between electrodes 16A and 16B. However, the notches 182 may provide some rotational movement 488 of electrode 16A about the axis 76 of the sensor 12F, while still maintaining the fixed distance 64 between the electrodes 16A and 16B. Thus, the notches 484 may allow for minor adjustment of the sensor 12F to take into account variations in the sizes of patients' heads.

As illustrated above, the shape of the substrate 56 around the electrodes 16 including the number of protrusions may vary. FIGS. 10A-10E illustrate different embodiments of the substrate 56 surrounding individual electrodes 16 for the sensor 12. These embodiments as illustrated may be designed for the substrate 56 surrounding electrode 16A, but in some embodiments may be altered for use with the substrate 56 surrounding the other electrodes 16B, 16C, and 16D. The different shapes of the substrate and protrusions and different number of protrusions in each embodiment of the electrode 16 may result in different distributions of the force load to reduce adhesion shear. Each substrate 56 surrounding each electrode 16 may include a body 568 having a top portion 570, a bottom portion 572, and side portions 574 and 576. Side portion 574 may be coupled to the bridge 72 of the sensor 12. In addition, each substrate 56 surrounding the electrode 16 may include a perimeter 578 and one or more protrusions 580.

Figure 10A:
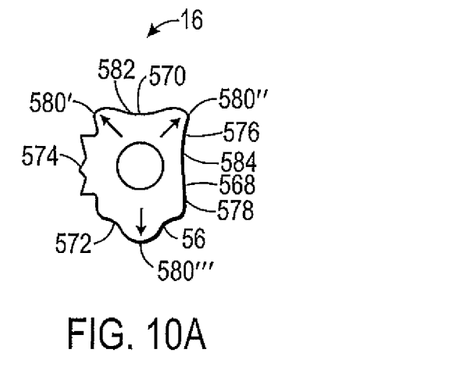
FIG. 10A is a top view of an embodiment of a single electrode of the sensor of FIG. 1.
Figure 10B:
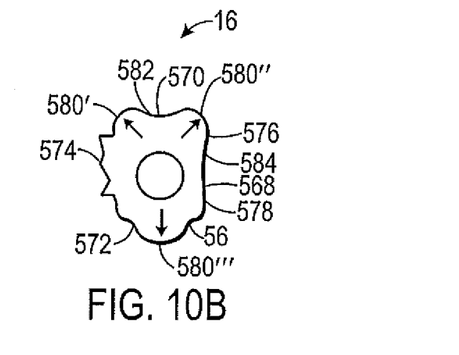
FIG. 10B is a top view of another embodiment of a single electrode of the sensor of FIG. 1.

The substrate 56 surrounding the electrodes 16 in FIGS. 10A and 10B may include a generally rectangular perimeter 578 with the top portion 570 and side portion 576 having slightly concaved curvatures 582 and 584 to form protrusions 580' and 580". In addition, the electrodes 16 in FIGS. 10A and 10B may include protrusion 580'" on the bottom portion 572. Protrusions 580' and 580" in FIG. 10B may include a broader and rounder shape than the same protrusions 580' and 580" in FIG. 10A, while protrusion 580'" in FIG. 10B may also be broader in shape than the same protrusion 580'" in FIG. 10A. The broader protrusions 580 in FIG. 10B may increase the surface area to better adhere the electrode 16 to the patient's skin. The protrusions 580 in both FIGS. 10A and 10B may distribute the load similarly in the directions indicated by the arrows to reduce adhesion shear.

Figure 10C:
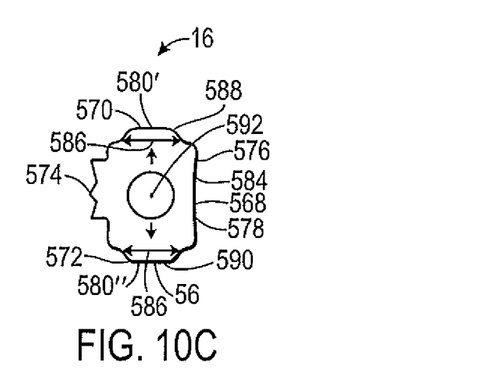
FIG. 10C is a top view of a further embodiment of a single electrode of the sensor in FIG. 1.

The substrate 56 surrounding electrode 16 in FIG. 10C may also include a generally rectangular perimeter 578 with the side portion 576 having slightly concaved curvatures 584. In addition, the substrate 56 surrounding the electrode 16 may include protrusions 580' and 580" on the top and bottom portions 570 and 572, respectively. The protrusions 580' and 580" may be tab shaped and include flat sides 588 and 590, respectively, and expand in width 586 from the sides 588 and 590 towards a center portion 592 of the body 568. The protrusions 580 may distribute the load in the directions indicated by the arrows to reduce adhesion shear. The wide tab shape may distribute the load over a greater area in the directions indicated to enhance the reduction of adhesion shear.

Figure 10D:
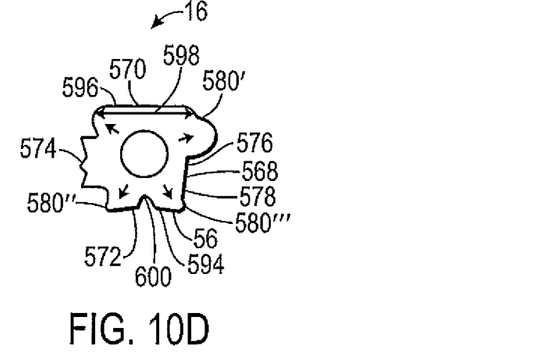
FIG. 10D is a top view of a yet further embodiment of a single electrode of the sensor in FIG. 1.

The substrate 56 surrounding electrode 16 in FIG. 10D may include a tooth-like perimeter 578 with bottom portion 572 and side portion 576 having slightly concaved curvatures 594 and 584. In addition, the substrate 56 surrounding the electrode 16 may include a flat side 596 on the top portion 570. The substrate 56 surrounding the electrode 16 may generally narrow in width 598 from the top portion 570 to the bottom portion 572, except where a protrusion 580' is located on the side portion 576. The substrate 56 surrounding the electrode 16 may also include a recess 600 dividing protrusions 580" and 580'" on the bottom portion 572. The protrusions 580 and shape of the body 568 may distribute the load in more directions indicated by the arrows than the other embodiments of the electrodes 16 to enhance reduction in adhesion shear. Also, the protrusion 580' may increase the surface area to better adhere the electrode 16 to the patient's skin.

Figure 10E:
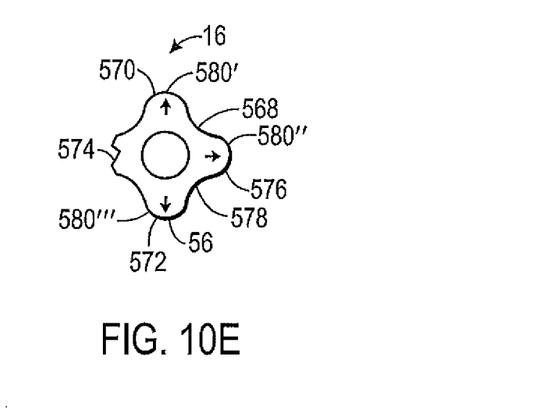
FIG. 10E is a top view of a still further embodiment of a single electrode of the sensor in FIG. 1.

The substrate 56 surrounding electrode 16 in FIG. 10E may include perimeter 578 similar in shape to substrate 56 surrounding electrode 16A of FIGS. 3, 7, and 9. In particular, the top portion 570, bottom portion 572, and side portion 576 may include protrusions 580', 580", and 580'", respectively. The protrusions 580', 580", and 580'" may include rounded lobes. The protrusions 580 may distribute the load in the directions indicated by the arrows to reduce adhesion shear. The shape of the body 568 may divide the load more evenly than the above embodiments of the bodies 568 of the substrate 56 surrounding the electrode 16. In addition, the shape may facilitate placement of the electrode 16 on the temple near the eye.

As mentioned above, the sensor 12 may need to be coupled to the patient 202 in a particular manner to ensure proper placement of the sensor 12. Instructions for sensor placement may be provided separately with the sensor 12 by the sensor manufacturer. In addition to or in lieu of manufacturer's instructions, instructions may be provided in a stepwise manner on the display 32 of the monitor 14. FIGS. 11-14 are representations of embodiments of help screens shown on the display 32 to verify placement of the electrodes 16 of the sensor 12. The screens may include text of the instructions for each step. Further, the monitor 14 may provide audible instructions as well.

Figure 11:
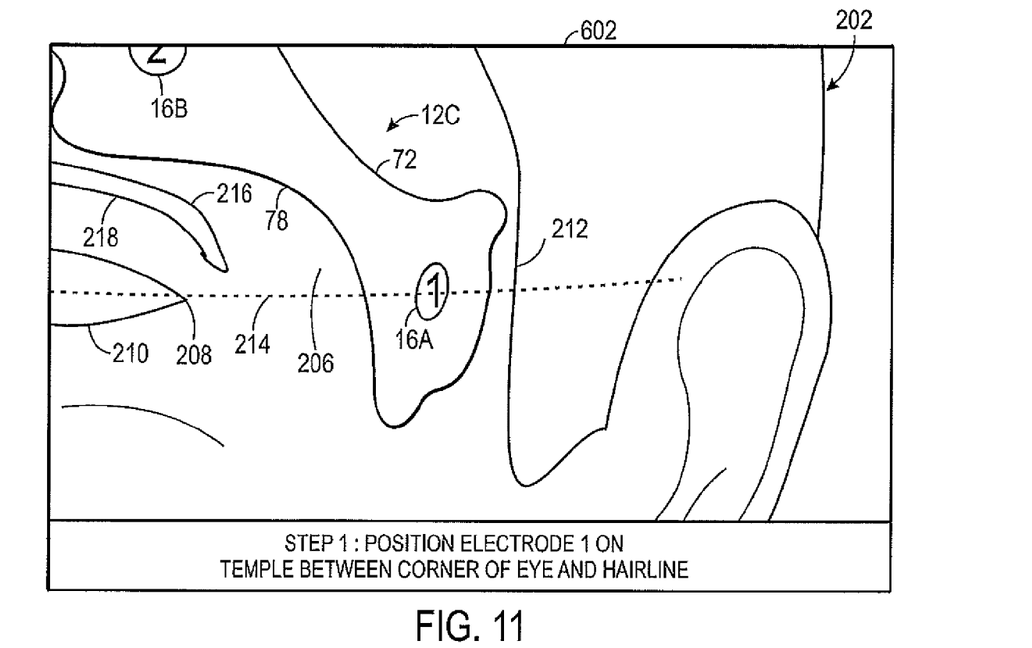
FIG. 11 is a representation of an embodiment of a help screen presenting a first step in positioning the sensor of FIG. 4 on the patient.
Figure 12:
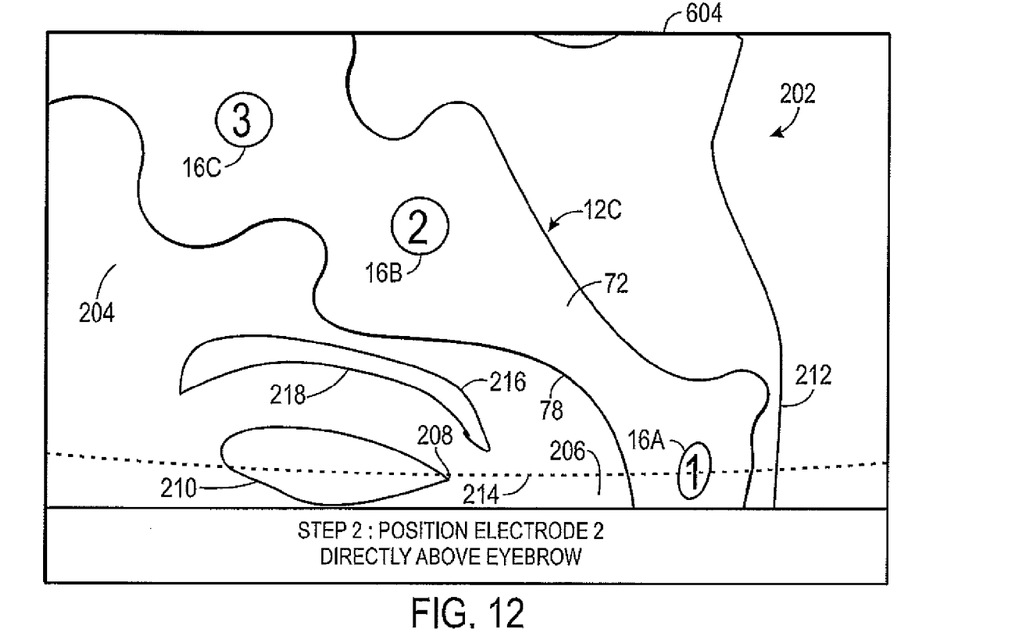
FIG. 12 is a representation of an embodiment of a help screen presenting a second step in positioning the sensor of FIG. 4 on the patient.
Figure 13:
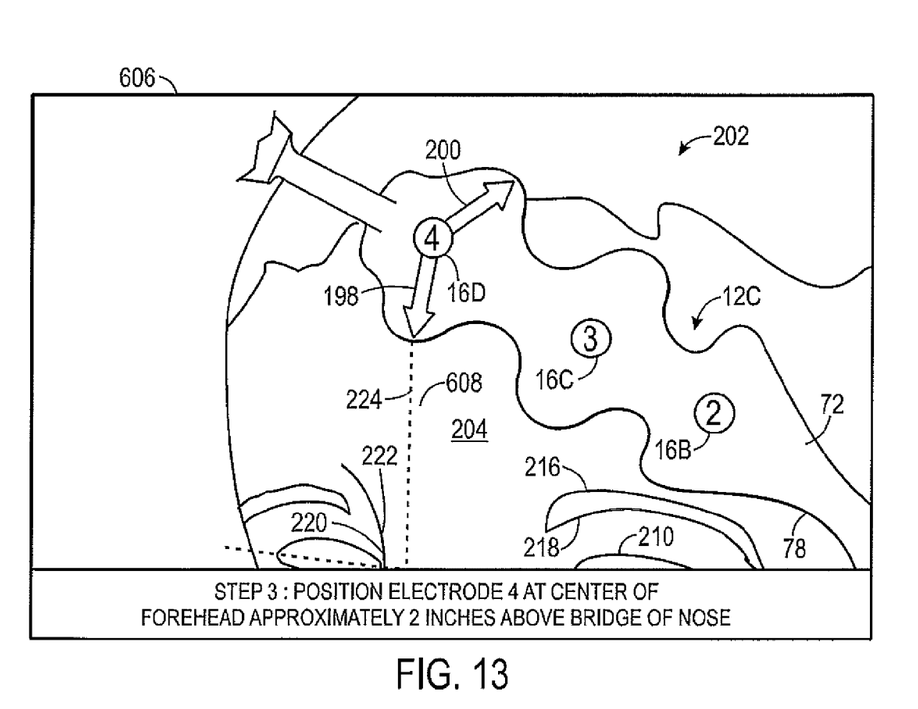
FIG. 13 is a representation of an embodiment of a help screen presenting a third step in positioning the sensor of FIG. 4 on the patient.

FIG. 11 may represent a help screen 602 for the first step that includes positioning the temple electrode 16A (e.g., labeled 1) on the patient's temple 206 between the corner 208 of the patient's eye 210 and the patient's hairline 212. The screen 602 may illustrate the alignment of the electrode 16A with the corner 208 of the eye 210 as indicated by the dashed line 214 (e.g., step 1). Upon attaching electrode 16A to the temple 206, the next step may include positioning electrode 1613 (e.g., labeled 2) adjacent temple electrode 16A directly above the top edge 216 of the eyebrow 218 as illustrated on help screen 604 in FIG. 12 (e.g., step 2). The screen 604 may illustrate the positioning of electrode 16B directly above the eyebrow 218. Upon attaching electrode 16B above the eyebrow 218, the next step may include positioning central forehead electrode 16D (e.g., labeled 4) adjacent electrode 16C (e.g., labeled 3) at a center 608 of the forehead 204 approximately 2 inches (5 cm) above the bridge 220 of the nose 222 (e.g., step 3) as illustrated on help screen 606 in FIG. 13. Positioning of the electrodes 16B and 16D may determine the position of electrode 16C by default. The screen 606 may indicate the positioning of electrode 16D at the center 608 of the forehead 204 by dashed line 224.

Figure 14:
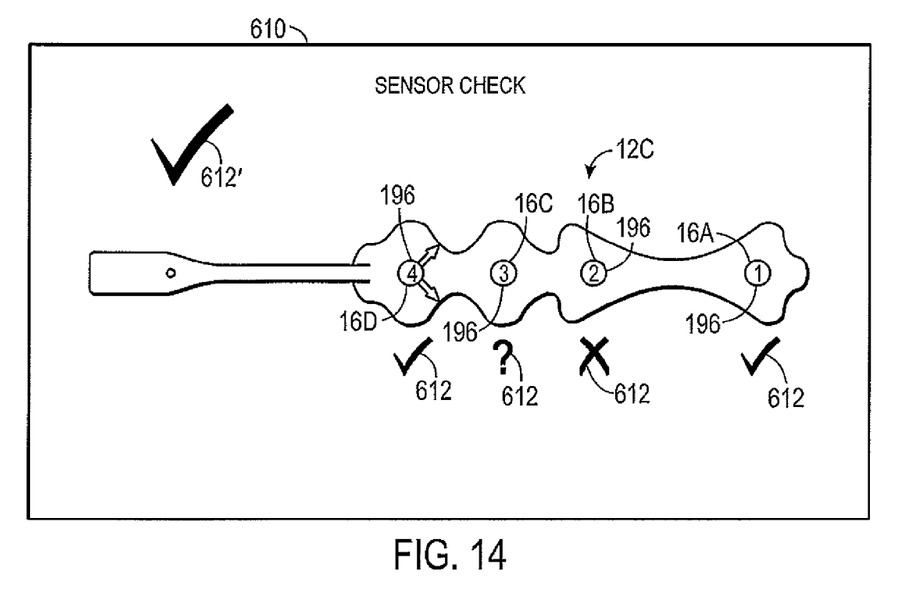
FIG. 14 is a representation of an embodiment of a help screen to verify placement of electrodes of the sensor of FIG. 4 on the patient.

As mentioned above, the monitor 14 may verify proper electrical contact or placement of the electrodes 16A, 16B, 16C, and 16D. FIG. 14 may represent a screen 610 of a sensor check for the proper electrical contact or placement of the sensor 12C. In certain embodiments, an indicator 612' (e.g., a large checkmark) may indicate a proper overall sensor placement of the device. As illustrated, the screen 610 may present the shape of the sensor 12C and each individual electrode 16. Alternatively, the screen 610 may list each individual electrode 16 in text. As illustrated, the each electrode 16 may include a label 196 to distinguish the electrodes 16, for example, numbers as previously described. In other embodiments, the labels 196 may include text to indicate the position of the electrode 16. For example, electrodes 16D, 16C, 16B, and 16A may be labeled C (center), G (ground), LE (left eye), and LT (left temple), respectively. In certain embodiments, electrodes 16B and 16A may be labeled RE (right eye) and RT (right temple), respectively. As illustrated, the status of each electrode 16 may be indicated by indicators 612. For example, the indicators 612 may include a checkmark (as shown with electrodes 16A and 16B) to indicate an acceptable range for electrode impedance and proper positioning for the electrode 16. Other indicators 612 may include an 'X' (as shown with electrode 16B) to indicate the electrode impedance is not within an acceptable range and the potential need to reposition the electrode 16. Further indicators 612 may include a question mark (as shown with electrode 16C) if the electrode impedance cannot be determined, for example, due to electrical interference. In certain embodiments, the indicators 612 may include text to indicate the status of each electrode 16. In other embodiments, the status of the electrodes 16 may be indicated by color coding the labels 196. For example, the colors may include green (equivalent to checkmark), red (equivalent to 'X'), or gray (equivalent to '?'). If certain electrodes 16 need attention, the indicator 612 and/or label 196 may blink. Upon an indication that one of the electrodes 16 needs attention, the positioning of the electrode 16 may be manually checked, as described above, to verify proper positioning. Then, the sensor check may be initiated again. Once all of the electrodes 16 are properly positioned, then monitoring may begin.

The above embodiments of the sensors 12 may be designed for adults and/or neonates. In addition, the embodiments of the sensors 12 may be designed to include different sizes (e.g., small, medium, large, etc.) for both adults and/or neonates. Further, the embodiments of the sensors 12 may be designed such that one size fits either most adults and/or neonates.

What is claimed is:

1. A bispectral index sensor comprising:
    an elongated substrate having:
    a first end portion and a second end portion and having a first electrode disposed on the first end portion and a second electrode disposed on the second end portion, the first electrode and the second electrode being separated from one another by a distance substantially equal to a distance from a patient's temple to a central portion of a patient's forehead, such that the first electrode is adapted to be placed on a patient's temple and the second electrode is adapted to be placed on the central portion of the patient's forehead;
    a third electrode and a fourth electrode disposed on the substrate in spaced apart relation between the first electrode and the second electrode, wherein the third electrode is positioned on the substrate to be placed on the patient's forehead directly above the patient's eye when the first electrode is placed on the patient's temple and the second electrode is placed on the central portion of the patient's forehead, the fourth electrode being positioned on the substrate between the second electrode and the third electrode and being adapted to be placed on the patient's forehead between the second electrode and the third electrode;
    wherein the elongated substrate has a width and a thickness, and wherein the substrate is sufficiently rigid in a direction along the width to prevent the electrodes from moving laterally relative to a longitudinal axis of the sensor and being sufficiently flexible along the thickness to facilitate bending of the substrate about a patient's head when the first electrode is placed on the patient's temple and the second electrode is placed on the central portion of the patient's forehead.

2. The sensor, as set forth in claim 1, wherein the substrate comprises an adhesive layer to facilitate attachment of the first electrode to the patient's temple and the second electrode to the central portion of the patient's forehead.

3. The sensor, as set forth in claim 1, wherein the elongated substrate has a length, wherein the length is substantially greater than the width and wherein the width is substantially greater than the thickness.

4. The sensor, as set forth in claim 1, wherein the substrate comprises a bridge disposed between the first electrode and the third electrode, wherein the bridge is configured to prevent the first and the third electrodes from moving laterally relative to the longitudinal axis of the sensor.

5. The sensor, as set forth in claim 4, wherein the bridge comprises a concave curvature configured to trace up and around lateral and top edges of an eyebrow of the patient to reinforce correct positioning of the first electrode and the third electrode.

6. The sensor, as set forth in claim 4, wherein the bridge comprises notches disposed at a mid-portion of the bridge, wherein the notches are configured to allow rotational movement of the first electrode about the longitudinal axis of the sensor.

7. The sensor, as set forth in claim 1, wherein the substrate surrounds the electrodes, the substrate surrounding the first and second electrodes includes protrusions configured to counteract peeling forces and to reduce adhesion shear.

8. The sensor, as set forth in claim 1, wherein the substrate surrounds the electrodes, the substrate surrounding each of the electrodes includes protrusions configured to counteract peeling forces and to reduce adhesion shear.

9. The sensor, as set forth in claim 1, wherein the substrate comprises a tail section on the second end portion which is coupled to an electrical cable and which is configured to resist lift-off in response to movement of the electrical cable.

10. The sensor, as set forth in claim 9, wherein the second end portion of the substrate proximate the second electrode comprises protrusions and a radiused cut out to separate the protrusions, wherein the protrusions are configured to provide forces to counteract lift-off of the tail section.

11. The sensor, as set forth in claim 10, wherein the tail section of the substrate comprises a knife-cut to separate the tail section from the protrusions.

12. The sensor, as set forth in claim 1, wherein the substrate comprises indicia to facilitate proper placement of the sensor on the patient, wherein the indicia comprises at least one arrow proximate the second electrode, the arrow being positioned to point toward a patient's nose when the first electrode is placed on the patient's temple and the second electrode is placed on the central portion of the patient's forehead.

13. A method for attachment of a bispectral index sensor to a patient, the method comprising:
    positioning a first electrode on a patient's temple;
    positioning a second electrode on a patient's forehead directly above a patient's eye;
    positioning a third electrode on a central portion of the patient's forehead; and positioning a fourth electrode on the patient's forehead between the second electrode and the third electrode, wherein the bispectral index sensor comprises a substrate supporting the electrodes and having a bridge disposed between the first and second electrodes, wherein the bridge is sufficiently rigid to prevent the first and the second electrodes from moving laterally relative to a longitudinal axis of the sensor.

14. The method, as set forth in claim 13, wherein the substrate has a width and a thickness, and the substrate is sufficiently rigid along the width to prevent the electrodes from moving laterally relative to the longitudinal axis of the sensor and sufficiently flexible along the thickness to facilitate bending of the substrate about the patient's forehead.

15. The method, as set forth in claim 13, wherein the substrate surrounds the electrodes, the substrate surrounding the first and the third electrodes comprises protrusions configured to counteract peeling forces and to reduce adhesion shear.

16. The method, as set forth in claim 15, wherein the substrate comprises a tail section which is coupled to an electrical cable, wherein the tail section of the substrate comprises a knife-cut to separate the tail section from at least one of the protrusions.

17. The method, as set forth in claim 13, wherein the bridge comprises notches disposed at a mid-portion of the bridge, wherein the notches are configured to allow rotational movement of the first electrode about the longitudinal axis of the sensor.

18. The method, as set forth in claim 13, wherein the bridge comprises a concave curvature configured to trace up and around lateral and top edges of an eyebrow of the patient to reinforce correct positioning of the first electrode and the second electrode.

19. The method, as set forth in claim 13, wherein the substrate comprises a second end portion proximate to the third electrode, the second end portion having a tail section coupled to an electrical cable, wherein the second end portion comprises protrusions and a radiused cut out to separate the protrusions.

20. A monitor comprising:
a display unit configured to display at least one help screen to facilitate a correct placement of a sensor on a patient, wherein the sensor comprises an elongated substrate having a first end portion and a second end portion and having a first electrode disposed on the first end portion and a second electrode disposed on the second end portion, the first electrode and the second electrode being separated from one another by a distance substantially equal to a distance from a patient's temple to a central portion of a patient's forehead, such that the first electrode is adapted to be placed on the patient's temple and the second electrode is adapted to be placed on the central portion of the patient's forehead, and a third electrode positioned on the substrate to be placed on the patient's forehead directly above a patient's eye when the first electrode is placed on the patient's temple and the second electrode is placed on the central portion of the patient's forehead, and a fourth electrode being positioned on the substrate between the second electrode and the third electrode and being adapted to be placed on the patient's forehead between the second electrode and the third electrode, wherein the at least one help screen comprises at least one help screen illustrating a representation of a portion of the patient's head and proper placement of the sensor on the portion of the patient patient's head.

21. The monitor, as set forth in claim 20, wherein the display unit is configured to display a first help screen illustrating positioning of the first electrode on the patient's temple, a second help screen illustrating positioning the third electrode directly above the patient's forehead directly above the patient's eye, and a third help screen illustrating positioning the second electrode on the central portion of the patient's forehead when the first electrode has been placed on the patient's temple and the third electrode has been placed on the patient's forehead directly above the patient's eye.

22. The monitor, as set forth in claim 20, wherein the display unit is configured to display a screen to verify a proper electrical contact or placement of the sensor on the patient.

23. The monitor, as set forth in claim 20, wherein the substrate has a length, a width, and a thickness, and is sufficiently rigid in a direction along the width to prevent the electrodes from moving laterally relative to a longitudinal axis of the sensor.

24. The monitor, as set forth in claim 20, wherein the substrate includes protrusions surrounding at least the first and the third electrodes, the protrusions being configured to counteract peeling forces and to reduce adhesion shear.

* * * * *